(12) United States Patent
Fiedotin et al.

(10) Patent No.: US 7,599,846 B2
(45) Date of Patent: Oct. 6, 2009

(54) METHOD FOR RENEWING MEDICAL PRESCRIPTIONS

(75) Inventors: Richard Alan Fiedotin, San Mateo, CA (US); Dan Zucker, Palo Alto, CA (US)

(73) Assignee: ePocrates, Inc., San Mateo, CA (US)

(*) Notice: Subject to any disclaimer, the term of this patent is extended or adjusted under 35 U.S.C. 154(b) by 0 days.

(21) Appl. No.: 11/838,055

(22) Filed: Aug. 13, 2007

(65) Prior Publication Data

US 2008/0046294 A1 Feb. 21, 2008

Related U.S. Application Data

(63) Continuation of application No. 09/643,554, filed on Aug. 22, 2000, now Pat. No. 7,286,996.

(51) Int. Cl.
*G06Q 10/00* (2006.01)
*G06Q 50/00* (2006.01)

(52) U.S. Cl. .............................. 705/2; 705/3

(58) Field of Classification Search ................. 705/2–3; 600/300
See application file for complete search history.

(56) References Cited

U.S. PATENT DOCUMENTS

| | | | |
|---|---|---|---|
| 4,847,764 A * | 7/1989 | Halvorson | 700/231 |
| 5,072,383 A | 12/1991 | Brimm et al. | |
| 5,737,539 A | 4/1998 | Edelson et al. | |
| 5,758,095 A | 5/1998 | Albaum et al. | |
| 5,772,585 A | 6/1998 | Lavin et al. | |
| 5,845,255 A | 12/1998 | Mayaud | |
| 6,021,392 A | 2/2000 | Lester et al. | |
| 6,076,166 A | 6/2000 | Moshfeghi et al. | |
| 6,493,427 B1 * | 12/2002 | Kobylevsky et al. | 379/67.1 |
| 7,286,996 B1 * | 10/2007 | Fiedotin et al. | 705/2 |

FOREIGN PATENT DOCUMENTS

| | | | |
|---|---|---|---|
| EP | 0921488 A1 * | 9/1999 | |
| WO | 95/29455 | 2/1995 | |

OTHER PUBLICATIONS

Biomerica and Viking Components Announce Strategic Partnership for Final Phase of ReadyScript, Jan. 2000, PR Newswire, p. 4796.*

* cited by examiner

*Primary Examiner*—Robert W Morgan
*Assistant Examiner*—Tran Nguyen
(74) *Attorney, Agent, or Firm*—Morgan, Lewis & Bockius LLP

(57) ABSTRACT

The invention provides a method for renewing a prescription for a pharmaceutical via an electronic network. A renewal request is generated for a renewal of a prior prescription. The request is transmitted to a prescriber for review and authorization. Once an authorized renewal prescription is received from the prescriber, a dispenser is notified to fill the renewal prescription.

20 Claims, 6 Drawing Sheets

FIG. 3

- Prescriber Memory — 320
- Operating System — 322
- Remote Access Procedures — 324
- Renewal Authorization Procedure — 326
- Renewal Database — 328
- Patient Profile 1 — 330(1)
- Patient Information — 332
- Prescription Profile 1 — 334(1)
- Prescribed Pharmaceutical — 336
- Prescriber — 338
- Dosage — 340
- Refill Details — 342
- Other Prescription Details — 344
- Prescription Profile N — 334(N)
- Patient Profile N — 330(N)
- Formulary Database — 350
- Drug-Drug Reaction Database — 352

FIG. 2

- Dispenser Memory — 120
- Operating System — 122
- Remote Access Procedures — 124
- Prescription Filling procedure — 126
- Dispenser database — 128
- Prescription 1 — 130(1)
- Patient Information — 132
- Drug ID / Name — 134
- Dosage — 136
- Prescribing Physician — 138
- Refill Details — 140
- Renewal Details — 142
- Prescription N — 130(N)
- Formulary Database — 146
- Drug-Drug Reaction Database — 148

METHOD FOR RENEWING MEDICAL PRESCRIPTIONS

CROSS-REFERENCE TO RELATED APPLICATIONS

This application is a continuation of U.S. patent application Ser. No. 09/643,554, entitled Method of Renewing Medical Prescriptions, filed Aug. 22, 2000 now U.S. Pat. No. 7,286,996, which is incorporated herein by reference.

TECHNICAL FIELD

The present invention relates generally to the pharmaceutical prescription industry, particularly to the renewal of pharmaceutical prescriptions.

BACKGROUND

A physician-patient meeting usually results in a diagnosis, with the physician writing a prescription for a pharmaceutical drug to treat the patient's diagnosed problem. In writing the prescription, the physician will ideally verify that the pharmaceutical drug is on formulary. The formulary is a list that informs prescribing physicians and pharmacists of the pharmaceuticals for which insurance providers will pay. The formulary may contain brand name or generic pharmaceuticals or both. In this regard, generic pharmaceuticals have the same active ingredients, strength, and dosage as their brand name counterparts, and are therapeutically equivalent to them.

In situations where patients have a chronic condition, such as high blood pressure or high cholesterol, the patient requires medication for a sustained period. An original prescription for a pharmaceutical drug to treat a chronic condition (a chronic medication), may include one or more refills authorizing the pharmacy to dispense additional medication in accordance with the original prescription without further authorization from the prescribing physician. Moreover, patients with chronic conditions often require the physician to re-prescribe or renew prescriptions for chronic medication over time. The original prescription typically contains the patient's name, the pharmaceutical's name, the prescribed dosage, and any renewal or refill information.

The original prescription is typically given to a pharmacy (whether retail, mail-order, on-line, or otherwise) that inputs the prescription information, along with the patient's pharmacy benefits and insurance information, into a computer and checks with the appropriate Pharmacy Benefit Management organization (PBM), or a PBM group at an insurance company, via telephone or on-line computer connection to ensure that the prescribed pharmaceutical drug is on the formulary.

PBMs track the prescriptions written by each physician who has a contracted with one or more of the health care plans affiliated with the PBM. PBMs administer prescription pharmaceutical claims, establish formularies, track physician prescribing patterns, provide education to improve their efficiency and cost effectiveness, and provide disease management programs. PBMs also seek to control the cost of prescription pharmaceuticals.

To lower the costs of prescription pharmaceuticals, PBMs negotiate prices on medications with pharmaceutical manufacturers. PBMs then determine price-performance profiles for every pharmaceutical on the market. Given that different pharmaceutical companies negotiate different prices with pharmaceutical manufacturers, the resulting price-performance profiles necessarily vary. For example, two pharmaceuticals for the treatment of high blood pressure will likely have two different price-performance profiles, each dependent upon the price a PBM pays the pharmaceutical manufacturer for the pharmaceutical.

Depending on its price-performance profile, a PBM will assign a status to each pharmaceutical on that PBM's formulary list. Typically, and by way of example, the statuses will be: preferred, approved, approved with prior authorization by the health insurance provider, available only if dispensed as a generic, and not approved. A pharmaceutical that has no formal status on a formulary or that has a "not approved" status is considered to be "off-formulary." The status of any particular pharmaceutical will, therefore, determine whether and to what extent a patient's health care plan will pay for the purchase of that pharmaceutical.

In addition to this use of formularies, some health care plans also provide physicians with a monthly pharmaceutical budget, financially penalizing physicians who go over budget and rewarding those physicians who are under budget. This is commonly referred to as "risk sharing" or "risk pooling."

For any number of reasons, PBMs revise their formularies frequently. As a result, there are often changes to the formulary that the patient and his physician may not be aware of. Thereafter, the patients might learn of the change only when advised by their pharmacist, or when they collect their prescription medication and notice a difference. Due to this late notice, there is frequently insufficient time to appeal or otherwise respond to the change.

PBMs communicate their formularies to physicians by mailing them binders containing formulary information every three to six months. Each health care plan has its own formulary so a physician may receive as many as one hundred different binders, though twenty to thirty is more typical. The content of the formulary is reinforced by a PBM "detail" force of PBM representatives who visit the physician periodically. Despite possessing the binders and the efforts of the "detail" force, physicians typically have a low compliance with the formularies.

For the most part, PBMs enforce their formularies at the pharmacy. When a patient submits a prescription, the pharmacist uses an on-line system to verify that the medication is listed on the patient's health care plan's formulary. If the medication is on-formulary, the pharmacy dispenses it, generally with a small co-payment by the patient. If it is off-formulary, and the prescribing physician has not authorized a generic substitute or a generic substitute does not exist, the patient either pays for the medication himself or the pharmacist calls the prescribing physician's office to request an alternative. This process is time consuming, and it requires the patient either to wait in the pharmacy or to return at a later time to obtain the medication.

Eventually, a patient with a chronic condition consumes the first supply of the prescribed medication. If the original prescription authorizes re-fills, the pharmacy will dispense a re-fill without further contact or authorization from the prescribing physician, assuming, of course, that the prescribed pharmaceutical remains listed on the formulary. If, however, the prescribed pharmaceutical is no longer listed on the formulary and the physician has not authorized a generic alternative, either the pharmacy must call the physician for a substitute or the patient must pay the full retail price for the off-formulary re-fill of the pharmaceutical (Under California law, PBMs must continue to pay for pharmaceuticals whose formulary status has changed). This process is repeated until the pharmacy dispenses the last authorized re-fill (if any), after which the patient or the pharmacy must contact the physician for a prescription renewal.

A renewal or re-prescription is a new prescription based at least in part upon the original prescription, i.e. for a pharmaceutical drug in the same therapeutic category (often the identical pharmaceutical drug), requiring a new authorization from the physician. While based on the therapeutic category of the pharmaceutical drug in the original prescription, the renewal prescription may change based upon revisions to the patient's insurance company's list of approved medications (the "formulary"), the patient's condition at the time of the renewal, or other factors.

Typically, a physician will have many patients with chronic health problems that require "chronic medications" (approximately 44%). As a result, substantial point-of-care inefficiencies arise in refilling and renewing prescriptions for chronic medications. Thus, on any given day, a physician will receive multiple calls requesting authorization for substitute pharmaceuticals that have changed formulary status in a re-fill or renewal situation. In the re-fill situation, the physician must take the time to determine an appropriate substitute that is on-formulary. In the renewal situation, the physician must take the time to evaluate several issues before authorizing a new prescription, namely: (1) whether the patient should continue taking the chronic medication; (2) whether to change any of the parameters of the prescription, e.g. brand or dosages; and/or (3) whether the chronic medication remains on-formulary and if not to identify a therapeutically equivalent pharmaceutical that is on-formulary.

In each case, the prescribing physician must deal with the inefficiencies attendant with the original prescription process, such as looking up the formulary status, dealing with a hard-copy of outdated formularies, reviewing the patient's records, etc. Additionally, because prescribing physicians typically must perform these duties at or very near the time of the pharmacy's telephone call, they are unable to address these issues efficiently, such as by addressing them in batches, verifying that a pharmaceutical is "preferred" by the PBM, etc.

These problems in dealing with formularies generate significant inefficiencies for the physician, and this translates into difficulties for PBMs seeking to control the costs for re-fill and renewal prescriptions. For example, physicians having to make rushed decisions when phoned for renewals are likely to default to the same chronic medication without checking the formulary to see if a different medication is now preferred by the PBM. Even if a chronic medication remains on-formulary, this is nonetheless a missed opportunity for a PBM to communicate its preferences to the prescribing physician because the physician has simply defaulted to the previously prescribed chronic medication without consulting the formulary list.

Preferred pharmaceuticals exist where PMBs have worked out special pricing or similar arrangements with pharmaceutical manufacturers. Therefore, despite the presence of more than a single medication on the formulary, PBMs might prefer one pharmaceutical over another. Even prescribing physicians who check the formulary are likely only to verify that the pharmaceutical is on-formulary, without determining whether that pharmaceutical is preferred by the PBM. Similarly, in the case of re-fills, a prescribing physician forced to determine an equivalent chronic medication that is on-formulary is not likely to determine whether a specific on-formulary pharmaceutical is preferred by the PBM over another therapeutically equivalent pharmaceutical.

Prescribing physicians have the responsibility to care for their patients, and, ultimately, they want to have more control over the decisions relating to their patient's care. PBMs and their formularies represent an intrusion into physicians' decision making processes and generate animosity among the physician community. As a result of this animosity, physicians are resistant to becoming more cooperative and compliant with the PBMs. This animosity, reluctance to comply with PBMs, and the missed communication opportunities between the PBMs and the prescribing physicians reduces compliance with formularies and decreases PBMs' flexibility to have more dynamic, cost efficient formularies.

Accordingly, there is a need in the art to increase the efficiency of using formularies at the point-of-care with a concomitant reduction of the intrusion in the decision-making process. Any improvement in the efficiency of the renewal prescription process would greatly assist in improving the overall efficiency of the prescription process as a whole. To this end, there is a need in the art for a system and/or method that will increase a physician's efficiency in handling renewal and/or refill prescriptions, especially for chronic medications.

SUMMARY OF THE INVENTION

The present invention provides a method for renewing a pharmaceutical prescription via an electronic network. The invention further permits prescribing physicians to review prescription renewal requests in batches, thereby increasing the efficiency of the process by reducing distraction caused by multiple calls for renewals. Additionally, it provides the prescribing physician with at-hand, up-to-date formulary information, drug-drug reaction information, patient specific information (e.g. patient's medical history), and low cost alternatives to facilitate the review, thereby reducing the time that is required to research this information using traditional methods.

A preferred embodiment of the present invention includes the steps of generating a request for the renewal of a prior prescription, transmitting the request to a prescriber for review and authorization, and receiving an authorized renewal prescription from the prescriber. A dispenser is then notified to fill the electronic renewal prescription. In a further embodiment of the present invention, the prescriber receives the electronic renewal request using an electronic device, such as a computer or a personal digital assistant, which request has specific data fields therein that point to information stored on the electronic device. This electronically stored information may facilitate the prescriber's review of the renewal request. More specifically, the electronically stored information includes, without limitation, formularies, pharmaceutical-pharmaceutical reaction data, and/or patient specific data. After reviewing the request, the prescriber may view the prescription or renewal, modify the request, and/or digitally sign and transmit the authorized renewal prescription back to the appropriate entity for fulfillment.

BRIEF DESCRIPTION OF THE DRAWINGS

For a better understanding of the nature and objects of the invention, reference should be made to the following detailed description, taken in conjunction with the accompanying drawings, in which:

FIG. 2 is a diagrammatic view of the dispenser memory shown in FIG. 1;

FIG. 3 is a diagrammatic view of the prescriber memory shown in FIG. 1;

Like reference numerals refer to corresponding parts throughout the several views of the drawings.

DETAILED DESCRIPTION OF PREFERRED EMBODIMENTS

The present invention provides a means for renewing a pharmaceutical prescription via an electronic network. As used herein, a pharmaceutical is defined as any chemical substance used in the diagnosis, treatment, or prevention of a disease, illness, medical condition, or as a component of a medication. A pharmaceutical may further be defines as any therapeutic product used in medicine, or a drug derived from organic or inorganic chemicals and used to treat a wide range of medical conditions.

Figure 1:
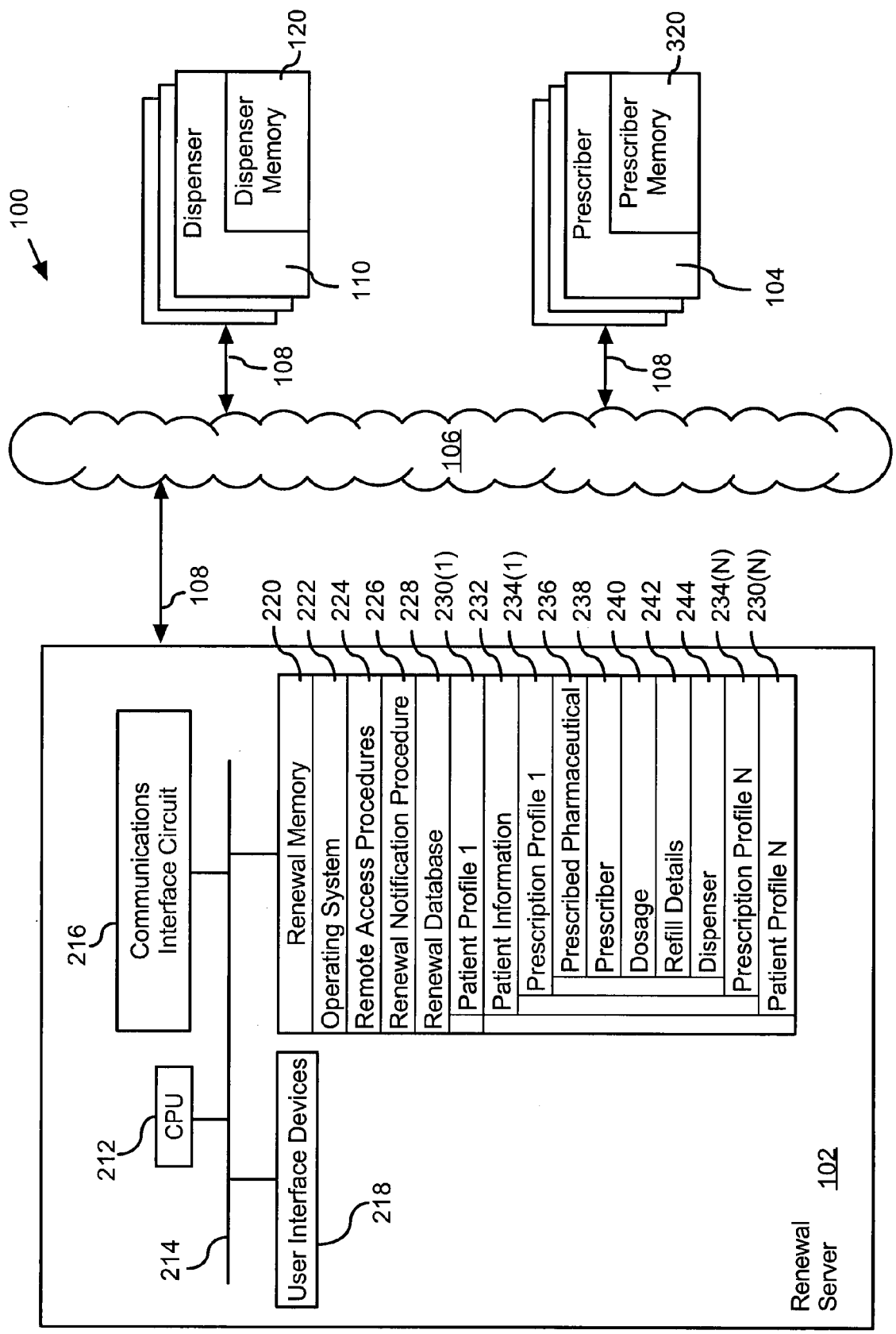
FIG. 1 is a diagrammatic view of an electronic network for renewing prescriptions in accordance with an embodiment of the present invention.

FIG. 1 is a diagrammatic view of an electronic network 100 for renewing prescriptions in accordance with an embodiment of the present invention. The network 100 comprises a series of points or nodes interconnected by communication paths. The network 100 may interconnect with other networks, may contain subnetworks, and may be embodied by way of a local area network (LAN), a metropolitan area network (MAN), a wide area network (WAN), or a global network (the Internet). The network 100 may further be characterized by the type of access service used, such as PSTN (Public Switched Telephone Network), ISDN (Integrated Services Digital Network), DSL (Digital Subscriber Line), ATM (Asynchronous Transfer Mode), T-carrier system, etc. In addition, network 100 may be characterized by the type of protocols used on it, such as WAP (Wireless Application Protocol), TCP/IP (Transmission Control Protocol/Internet Protocol), NetBEUI (NetBIOS Extended User Interface), or IPX/SPX (Internetwork Packet Exchange/Sequenced Packet Exchange). Additionally, the network 100 may be characterized by whether it carries voice, data, or both kinds of signals; by who can use the network 100 (whether it is public or private); and by the usual nature of its connections (e.g. dial-up, dedicated, switched, non-switched, or virtual connections).

The network 100 connects a plurality of pharmaceutical dispensers 110 and authorizing prescribers 104 to at least one renewal server 102. This connection is made via a communication or electronic network 106 that, as mentioned previously, may comprise an Intranet, wireless network, or preferably the Internet. The connection is made via communication links 108, which may, for example, be coaxial cable, copper wire (including PSTN, ISDN, and DSL), optical fiber, wireless, microwave, or satellite links. Communication between the prescriber, dispenser, and the renewal server preferably occurs via Internet protocol (IP) or an optionally secure synchronization protocol, but may alternatively occur via electronic mail (email).

As used herein, a dispenser is a retail-store pharmacy, a mail-order pharmacy, an on-line pharmacy, a PBM acting as a pharmacy, a PBM acting in conjunction with any of the former, or any entity or person authorized to dispense prescription pharmaceuticals. As used herein, an authorizing prescriber is a person having the authority to authorize a dispenser to dispense a pharmaceutical. Depending on the laws of any particular jurisdiction, such a person includes, without limitation, physicians, physician assistants, registered nurses, or persons acting under the direction of these individuals.

The renewal server 102 is shown in FIG. 1, and is described below as being distinct from the dispensers 110. The skilled artisan will, however, appreciate that the renewal server 102 and the dispensers 110 may be one and the same without deviating from the scope of the present invention.

The renewal server 102 comprises at least one data processor or central processing unit (CPU) 212, a renewal memory 220, user interface devices 218, a communications interface circuit 216, and at least one bus 214 that interconnects these elements. The renewal memory 220 includes an operating system 222 (such as DOS, UNIX™, Windows™, Linux™, OS/2™, AS/400™, PalmOS™, AIX™, NEXTSTEP™, OS/390™, OS/9™, OS/9000™, VMS™, CP/M™, Solaris™, or MacOS™), which may store instructions for communicating, processing data, accessing data, storing data, searching data, etc. The renewal memory 220 also includes remote access procedures 224 and a renewal notification procedure 226.

The renewal memory 220 further includes a renewal database 228 preferably containing a plurality of patient profiles 230(1) and 230(N). Each patient profile 230(1) and 230(N) preferably contains patient information 232, such as contact details, information concerning the patient's medical history, the patient's medical insurance details, etc. Preferably, each patient profile 230(1) and 230(N) also contains a number of prescription profiles 234(1) and 234(N) for that particular patient. Each prescription profile 234(1) and 234(N) also preferably contains information such as a prescribed pharmaceutical identifier 236, a prescriber identifier 238, the dosage 240 of the prescribed pharmaceutical, refill details 242, and a dispenser identifier 244. An identifier is any means serving to identify, indicate, or name a body of data.

The dispensers 110 and prescribers 104 access the communication network 106 via remote client computing devices, such as desktop computers, laptop computers, notebook computers, handheld computers, personal digital assistants (PDA's), or the like. The prescribers 104 preferably use PDA'S, as they are typically not desk bound, while dispensers 110 typically use desktop computers. The PDA's are preferably wireless, but may alternatively synchronize with a desktop computer that is itself connected to the communication network or may themselves connect to the communication network 106 via a wired connection.

The dispensers' and prescribers' computing devices, 110 and 104 respectively, preferably also include a data processor or central processing unit (CPU), user interface devices, communications interface circuits, and buses, similar to those described in relation to the renewal server 102. The dispensers 110 and the prescribers 104 also include memories 120 and 320 respectively, described below. Memories 220, 120, and 320 may include both volatile memory, such as random access memory (RAM), and non-volatile memory, such as a hard-disk.

FIG. 2 is a diagrammatic view of the dispenser memory 120 shown in FIG. 1. The dispenser memory 120 includes an operating system 122 and remote access procedures 124 compatible with the remote access procedures 224 (FIG. 1) in the renewal server's memory 220 (FIG. 1). Preferably, the dispenser memory 120 also includes a prescription filling procedure 126 for receiving electronic prescription requests and filling such requests (prescriptions and refills thereof). Furthermore, the dispenser memory 120 preferably also includes a dispenser database 128 containing a plurality of prescriptions identified by unique prescription identifiers 130(1) and 130(N). Each prescription 130(1) and 130(N) preferably contains patient information 132, such as contact details, information concerning the patient's medical history/records, the patient's medical insurance details, the patient's physician(s), etc. Each prescription 130(1) and 130(N) also preferably contains an pharmaceutical identifier 134, a prescribed dosage 136 for the prescribed pharmaceutical, a prescriber identifier 138, refill details 140, and renewal details 142. The refill details 140 preferably include the number of refills remaining and the date the last refill will be consumed and a date at which the refill will expire. The renewal details 142 preferably include a renewal date and a date at which the renewal will expire.

The dispenser memory 120 preferably also includes a formulary database 146 and a drug-drug reaction database 148, or a pointer thereto. Formulary database 146 includes, for example and without limitation, pharmaceutical identifiers and their associated formulary status (preferred, on-formulary, generic substitute permitted, or off-formulary).

FIG. 3 is a diagrammatic view of the prescriber memory 320 shown in FIG. 1. The prescriber memory 320 includes an operating system 322 and remote access procedures 324 compatible with the remote access procedures 224 (FIG. 1) in the renewal server's memory 220 (FIG. 1). The prescriber memory 320 preferably also includes a renewal authorization procedure 326 for creating and transmitting an authorized renewal prescription. The prescriber memory 320 preferably also include a renewal database 328 containing a plurality of patient profiles 330(1) and 330(N). Each patient profile 330(1) and 330(N) preferably contains patient information 332, such as contact details, information concerning the patient's medical history, the patient's medical insurance details, the patient's physician(s), and the like.

Each patient profile 330(1) and 330(N) also preferably contains a number of prescription profiles 334(1) and 334(N) for that patient. Each prescription profile 334(1) and 334(N) preferably contains information such as a prescribed pharmaceutical identifier 336, a prescriber identifier 338, the prescribed dosage 340 for the pharmaceutical, refill details 342, and a dispenser identifier 344. As described in co-pending application Ser. No. 09/487,932 filed Jan. 20, 2000, which is incorporated in its entirety herein by reference, the prescriber memory 320 preferably also includes a formulary database 350 and a drug-drug reaction database 352. The formulary database 350 and a drug-drug reaction database 352 are periodically updated by the renewal server.

It should be noted that the various databases described above have their data organized in a manner so that their contents can easily be accessed, managed, and updated. The databases may, for example, comprise flat-file databases (a database that takes the form of a table, where only one table can be used for each database), relational databases (a tabular database in which data is defined so that it can be reorganized and accessed in a number of different ways), or object-oriented databases (a database that is congruent, with the data defined in object classes and subclasses). The databases may be hosted on a single server or distributed over multiple servers. For ease of explanation, prescription data fields in any of the abovementioned databases will be referred to as prescription records.

Figure 4:
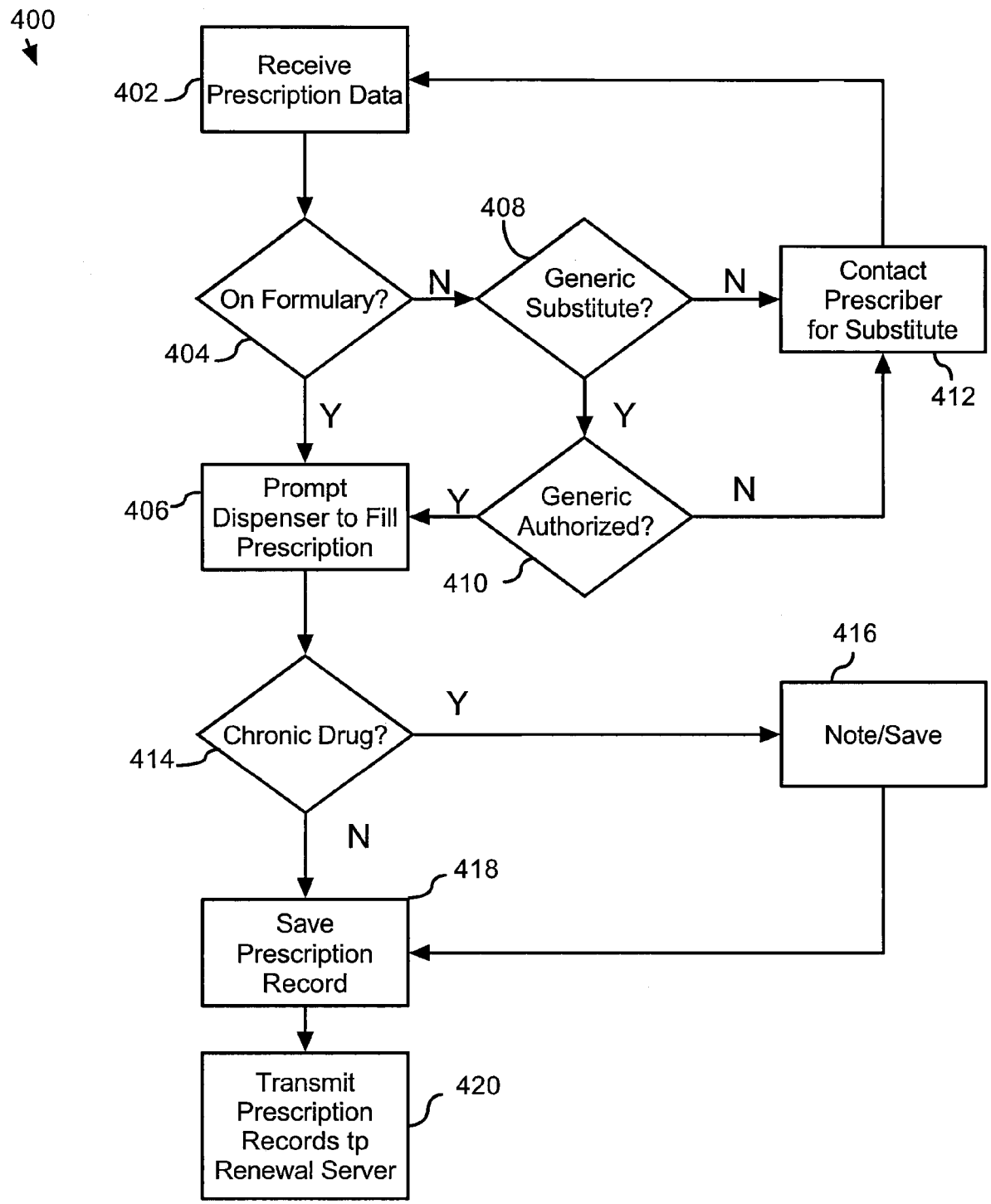
FIG. 4 is a flow chart showing a dispenser side method for filling original prescriptions in accordance with an embodiment of the present invention.

FIG. 4 is a flow chart showing a dispenser side method 400 for filling original prescriptions in accordance with an embodiment of the present invention. The prescription filling procedure (126 of FIG. 2) begins by receiving, at 402, an original prescription containing prescription data, including at least a pharmaceutical identifier, a patient identifier, a prescriber identifier, the prescribed pharmaceutical dosage, and refills details. Receipt of the original prescription may occur in a number of ways, such as electronically, by fax machine, by email, by postal mail, or by hand.

If the original prescription is received by hand, the details of the original prescription are captured manually and stored in the dispenser database (128 of FIG. 2), where the prescription is referenced by a unique prescription identifier (130 of FIG. 2). If the original prescription is received electronically, it is preferably captured automatically and stored in the dispenser database (128 of FIG. 2), where the prescription is referenced by a unique prescription identifier (130 of FIG. 2).

The formulary status of the prescribed pharmaceutical is then checked, at 404, by referencing the formulary database (146 of FIG. 2). If the prescribed pharmaceutical is on the formulary list, the dispenser will be prompted, at 406, to dispense the pharmaceutical in accordance with the prescription. If the prescribed pharmaceutical is not on the formulary list, the procedure checks, at 408, whether a generic substitute is on the formulary list, at 408, and if a generic substitute is on the formulary list, whether the prescriber has authorized the use of a generic substitute, at 410. If a generic substitute is not on the formulary list or if the prescriber has not authorized a generic substitute, a notice is posted to contact the prescriber and request that he prescribe a substitute pharmaceutical, at 412.

After the original prescription has been filled, it is determined whether the prescribed pharmaceutical is a chronic medication, at 414. If the prescribed pharmaceutical is a chronic medication, the renewal method according to the invention notes and saves this fact, at 416. The prescription records in the dispenser database (128 of FIG. 2) are then updated, at 418. The updated prescription records are finally transmitted to the renewal server, at 420.

Figure 5:
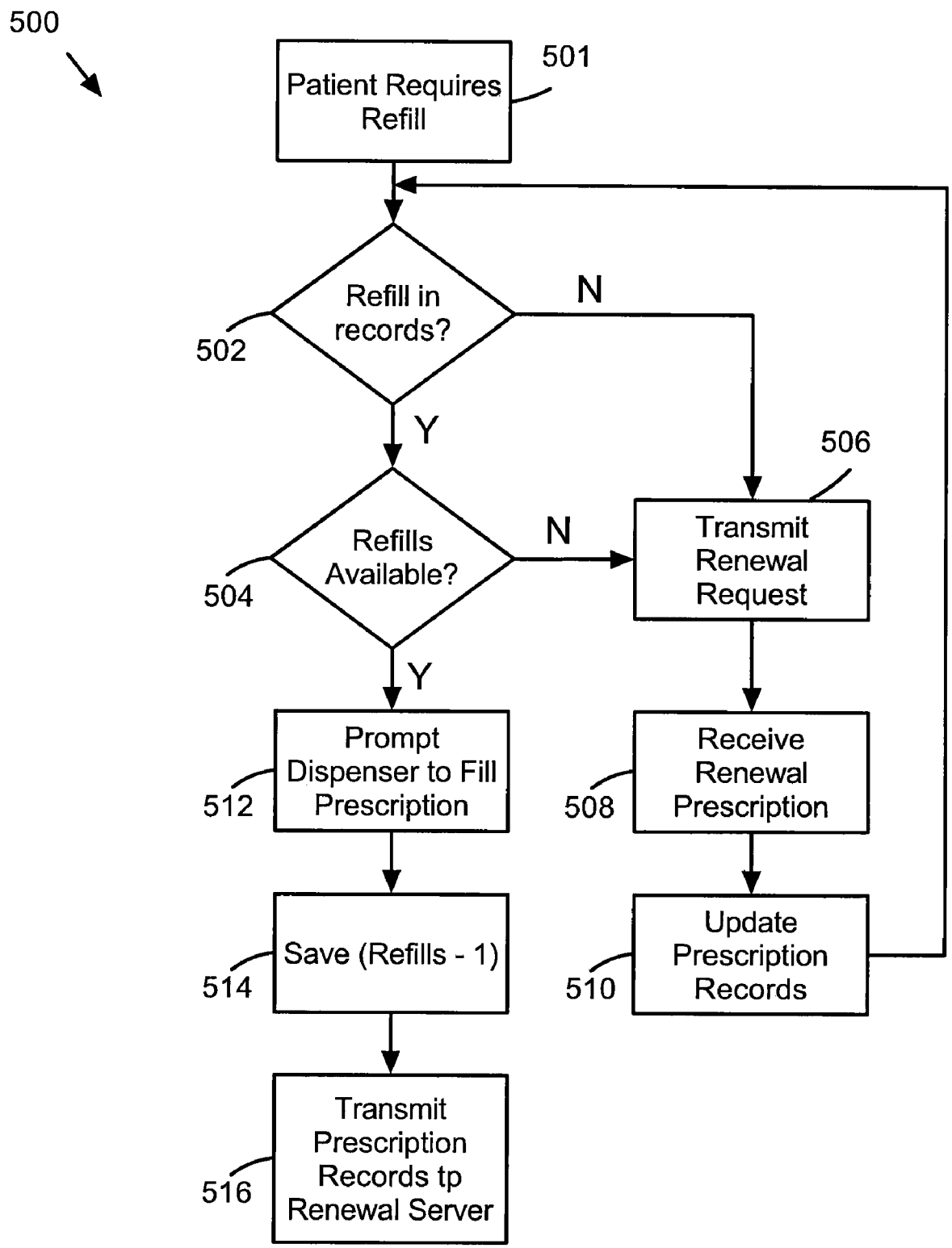
FIG. 5 is a flow chart showing a dispenser side method for filling a refill and authorized renewal prescriptions in accordance with an embodiment of the present invention.

FIG. 5 is a flow chart showing a dispenser side method 500 for filling a refill and authorized renewal prescriptions in accordance with an embodiment of the present invention. When a patient orders a refill at a dispenser, at 501, the prescription filling procedure (126 of FIG. 2) checks, at 502, whether that refill prescription exists in its records. If the refill prescription exists, the prescription filling procedure checks whether there are any refills remaining available on that particular prescription, at 504.

If there is no refill prescription in the records, or if no refills remain on the prescription, the dispenser transmits a renewal request to the renewal server, at 506, i.e. a prescription renewal request is created before the expiration of the original or prior prescription. The prescription renewal request preferably includes a patient identifier, a pharmaceutical identifier, a dispenser identifier, a prescription identifier, a prescriber identifier, a dosage, number of refills, and a strength.

If a refill is available, the dispenser is prompted to fill the prescription, at 512. The system then deducts one refill from the total amount of refills prescribed and saves this information, at 514, in the prescription records in the prescription database (128 of FIG. 2). The dispenser then transmits the updated prescription records to the renewal server, at 516. Once prescribers authorize a renewal prescription, discussed in relation to FIG. 7, the dispenser receives the renewal prescription, at 508, and updates its prescription records, at 510.

Figure 6:
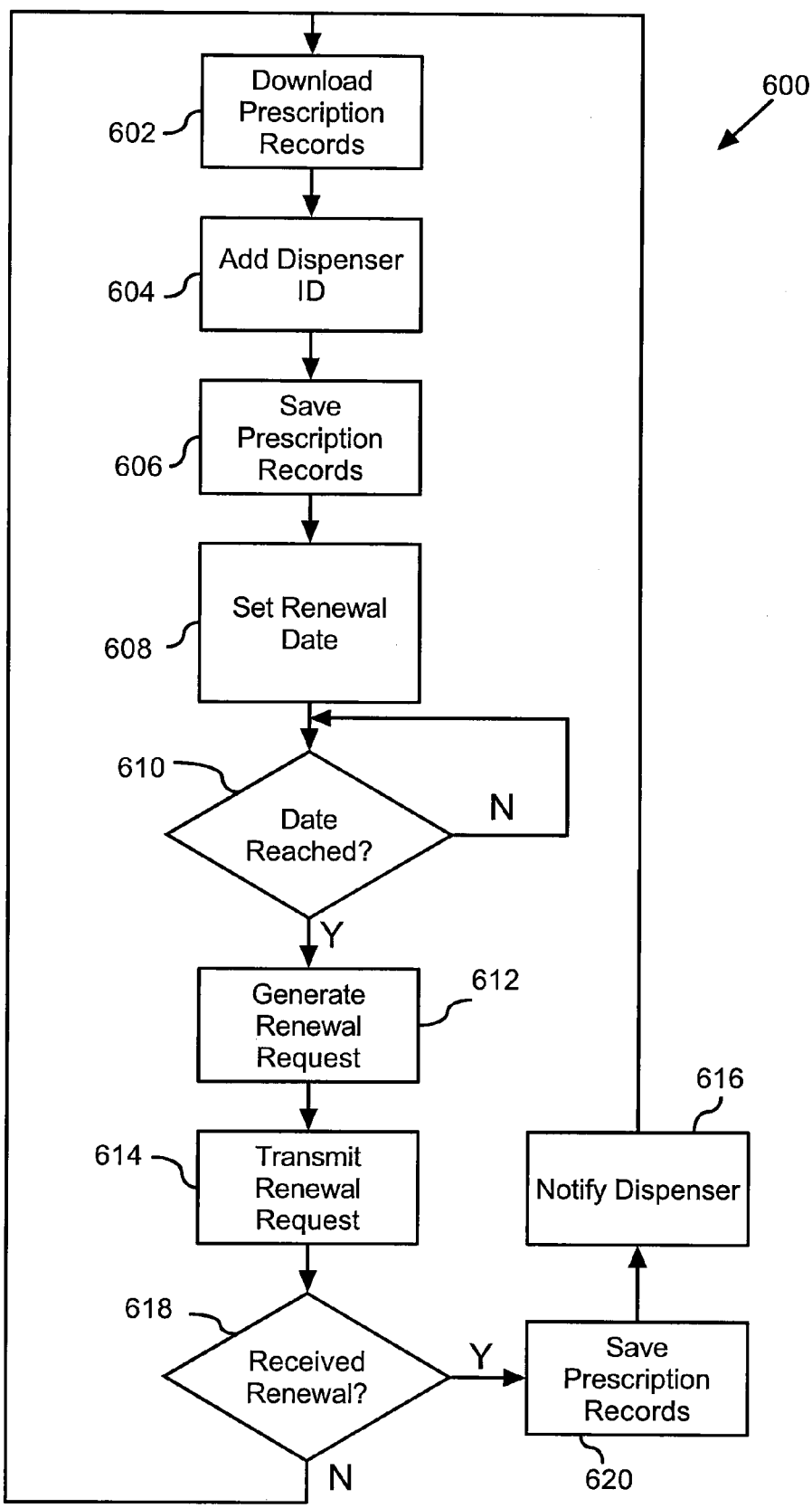
FIG. 6 is a flow chart showing a renewal server side method used to generate and transmit a request for a renewal prescription in accordance with an embodiment of the present invention.

FIG. 6 is a flow chart showing a renewal server side method 600 used to generate and transmit a request for a renewal prescription in accordance with an embodiment of the present invention. The renewal notification procedure (226 of FIG. 1) downloads, at 602, current prescription records from the dispenser (110 of FIG. 1) and saves the prescription records to the renewal database (230 of FIG. 1). The renewal database adds a dispenser identifier (246 of FIG. 1) to the prescription records, at 604. The prescription records are then saved to the renewal database, at 606.

The renewal notification procedure then calculates when the prescribed refills will run out, and sets a renewal date a set time prior to the date when the prescribed refills will run out, such as three weeks before such a date. The renewal notification procedure then periodically determines whether the renewal date has been reached, at 610. Once the renewal date has been reached, a renewal prescription request is generated, at 612, and transmitted to the prescriber responsible for prescribing the original prescription, at 614, or any other prescriber specified. Safety precautions are preferably incorporated so as to avoid a single renewal request being sent to multiple prescribers. The prescriber then deals with the renewal request as discussed in relation to FIG. 7. Once the prescriber has renewed a prescription and transmitted the renewed prescription back to the renewal server, it is received, at 618, and the new renewal details are saved into the prescription records, at 620. The dispenser is then notified to fill the renewal prescription, at 616. It should be noted that refills, renewal requests, and renewal prescriptions preferably expire after a predetermined time period.

Figure 7:
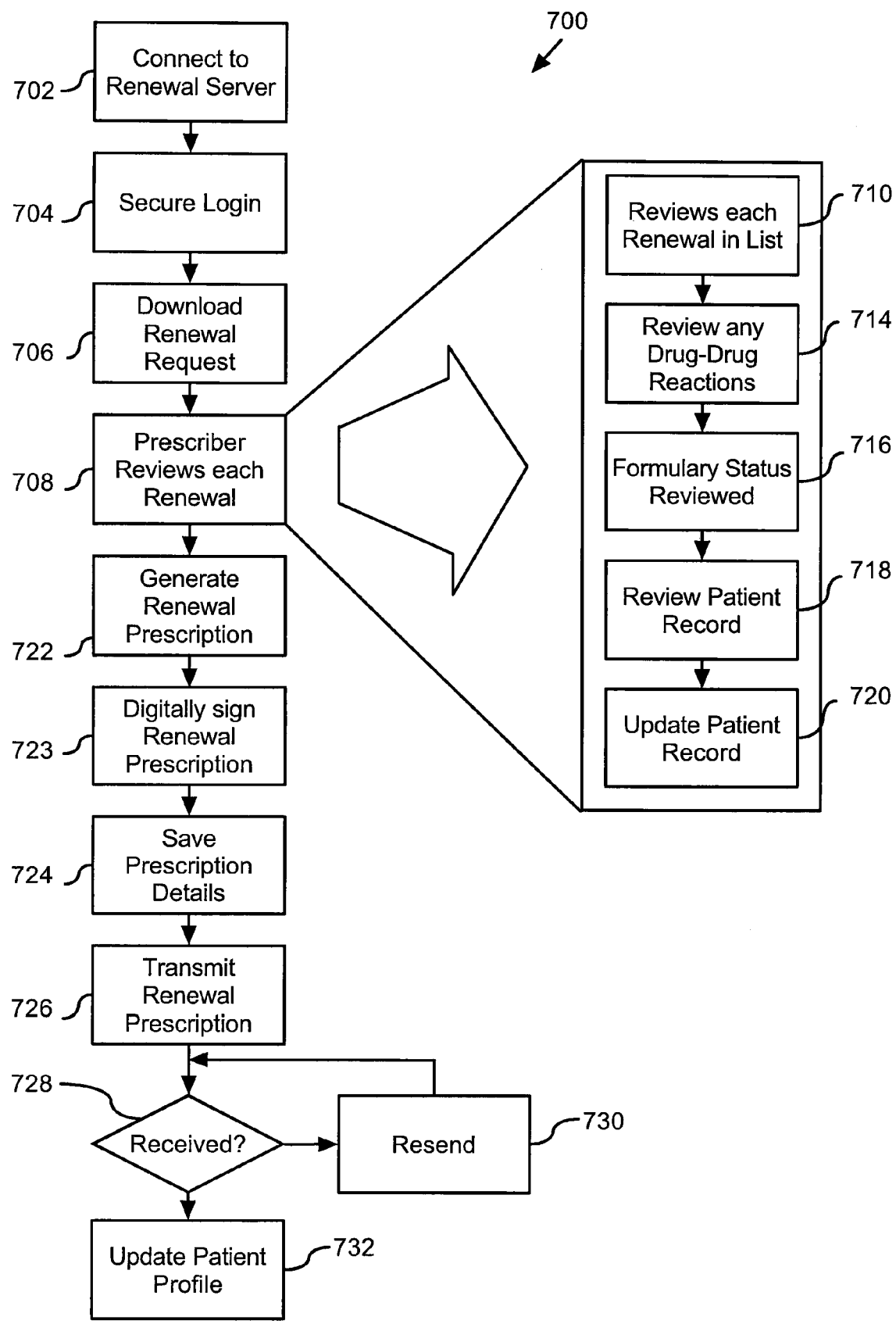
FIG. 7 is a flow chart showing the prescriber side method for authorizing a renewal prescription in accordance with an embodiment of the present invention.

FIG. 7 is a flow chart showing a procedure for authorizing a renewal prescription in accordance with an embodiment of the present invention. The prescriber (104 of FIG. 1) connects to the electronic network (106 of FIG. 1), more specifically the renewal server (102 of FIG. 1), at 702. The prescriber then securely logs into the renewal server, at 704. Preferably, the secure login occurs automatically when the prescriber synchronizes his PDA with his desktop computer, but may also occur manually by having the prescriber enter a unique username and password or digital certificate and secret signing key, or the like.

The prescriber's computing device (104 of FIG. 1) then downloads, preferably automatically during synchronization, all renewal request(s) directed to that prescriber, at 706. The prescriber may at this time, or at any other time between successive synchronizations, review the renewal requests, at 708, and deal with the requests in a batch mode or, if preferred, piecemeal.

In addition to reviewing the information provided in the renewal request itself, at 710, additional information may be provided to the prescriber to assist in the decision making process. The renewal authorization procedure (326 of FIG. 3) displays such additional information using a prescribed pharmaceutical identifier (336 of FIG. 3), a patient profile (330 of FIG. 3), and/or a dispenser identifier (344 of FIG. 3). The additional information preferably includes, without limitation, a drug-drug reaction database (354 of FIG. 3), at 714, a formulary database (350 of FIG. 3), at 716, patient medication history, and/or low cost therapeutic alternatives. It will be recognized that these databases may be separate or combined.

Alternatively, additional information may be added to the renewal request by the renewal server (102 of FIG. 1) and transferred to the prescriber therewith. The formulary database (350 of FIG. 3) then preferably provides the prescriber with generic substitutes, brand name substitutes, and/or PBM preferences in addition to the formulary status of the pharmaceutical prescribed in the prescription up for renewal.

Additionally, the patient identifier and/or the unique prescription identifier points to the patient profile (330 of FIG. 3) that will provide the prescriber with relevant patient information, such as previous prescriptions, or comments and notes useful to the prescriber, at 718. If the prescriber makes any changes, the patient's medical profile is updated, at 720. As part of the review process, the prescriber may want to, or may be required to, contact the patient for further consultation, after which the prescriber may update that patient's profile (330 of FIG. 3) with further comments. Contacting the patient may take the form of making a notation on the PDA, such as clicking on an "Ask patient to contact me" button, which ultimately is communicated to the renewal server. The patient is then contacted by back office staff, or alternatively the dispenser is contacted, to notify the patient to contact the prescriber. This may take the form of a telephone call, email, postal mail, facsimile, or the like.

A skilled artisan will recognize that the transfer of the renewal request 706 may occur using many different sets of steps other than those described above without deviating from the scope of the present invention. For example, and without limitation, the renewal server (102 of FIG. 1) could contact the prescriber's computing device or PDA to initiate the transfer of data. The ultimate result is that the prescriber has the renewal request(s) in an electronic format resident on his computer and/or PDA, such that the prescriber may review each notification at a time convenient and efficient for the prescriber.

After reviewing the renewal request, the renewal authorization procedure (326 of FIG. 3) generates an electronic renewal prescription, at 722. The electronic renewal prescription preferably includes at least a patient identifier, a pharmaceutical identifier, a prescribed dosage, a prescriber identifier, and refill details. It should be noted that the renewed prescription may have different components to the prior prescription initially prescribed. The prescriber then authorizes the renewal prescription using a digital signature, typically using an algorithm such as that provided by Certicom™ 723, and the record is saved in an authorized renewal prescription database (328 of FIG. 3), at 724.

The authorized renewal prescription is then transmitted to the renewal server for further processing, at 726. The renewal authorization procedure (326 of FIG. 3) waits for a notification from the renewal server that the authorized renewal prescription was in fact received, at 728. If it was not, the prescriber is prompted to rectify the situation (e.g., re-send the renewal prescription or call the renewal server service directly), at 730. If it was received, the patient profile (232 of FIG. 1) is updated accordingly. The prescriber then preferably notifies the patient that the renewal has been authorized.

The renewal server, prescriber, and/or dispenser periodically share updates of the status of the prescription renewal requests. The status is preferably ascertained by the renewal which determines how many prescription renewal requests were transmitted to the prescriber and establishes how many of the prescription renewal requests the prescriber has reviewed. The status is then preferably sent by the renewal server to the prescriber.

It is anticipated that the prescriber will contact the renewal server periodically, and would download multiple renewal requests at one time for review at the prescriber's convenience. It is also anticipated that the prescriber will transmit multiple authorized renewal prescriptions, rather than a single renewal request, each time he completes a review. It is in this manner that the prescriber may receive multiple requests for renewal prescriptions without receiving telephone calls from patients or pharmacies, may review the requests batch-wise, may contact patients for consultations at times convenient to the prescriber, and may check formularies. Wireless technologies permit PDAs to electronically transfer the data without the need of a wired connection.

The foregoing description, for purposes of explanation, used specific nomenclature to provide a thorough understanding of the invention. Nevertheless, the foregoing descriptions of the preferred embodiments of the present invention are presented for purposes of illustration and description and are not intended to be exhaustive or to limit the invention to the precise forms disclosed; obvious modifications and variations are possible in view of the above teachings. Modern computer equipment and software facilitate numerous configurations of the various aspects of the present invention without deviating from the scope of the invention. For example, it does not matter whether the renewal server is part of or separate from the dispenser server. Furthermore, much of the data transfer can take place in either direction, while still accomplishing the desired end, e.g., transfer of information to a specific place. In addition, the various databases may be replaced by a central database. The renewal server, dispenser and prescriber then access the centralized database to obtain data. Access to the centralized database preferably occurs in real time via "always-on" connections. A skilled artisan will readily recognize that these and many other insubstantial variations of the preferred embodiments described above may be implemented without deviating from the scope of the present invention, as defined below.

What we claim is:

1. A system for renewing a prescription for a pharmaceutical via an electronic network, the system comprising:
   a renewal server comprising:
      a processor;
      a communications interface circuit for communicating with a prescriber and a dispenser over a network, where the dispenser comprises a pharmacy or pharmacy benefit organization; and
      a memory comprising:
         an operating system;
         a database comprising at least one patient profile that includes:
            an identifier of a patient; and
            at least one prescription associated with the identifier of the patient, the at least one prescription comprising:
               a prescribed pharmaceutical;
               an identification of a prescriber that prescribed the prescribed pharmaceutical; and
               an expiration date of the prescription; and
   wherein the renewal server is capable of:
      monitoring the expiration date by periodically determining whether a predetermined time period before the expiration date has been reached;
      generating a prescription renewal request for renewal of the prescription prior to the expiration date based on the monitoring, where the generating occurs without human intervention;
      transmitting the prescription renewal request via an electronic network to the prescriber having authority to authorize the dispenser to dispense the prescription;
      receiving a renewal prescription at the renewal server, in response to the prescription renewal request, from the prescriber; and
      notifying the dispenser to fill the renewal prescription.

2. The system of claim 1, wherein the prescriber uses a prescriber computing device comprising:
   a processor;
   a communications interface circuit for communicating with the renewal server and the dispenser over the network; and
   a prescriber memory comprising:
      an operating system;
      a renewal database comprising at least one patient profile comprising:
         the identifier of the patient;
         the prescribed pharmaceutical;
         the prescriber of the prescribed pharmaceutical; and
         the expiration date of the prescription; and
      remote access procedures to receive a prescription renewal request from the renewal server and to transmit the prescription renewal to the renewal server.

3. The system of claim 2, wherein the prescriber memory further comprises:
   procedures for displaying the prescription renewal request; and
   procedures for generating a renewal prescription based at least in part on the renewal request.

4. The system of claim 3, wherein the prescriber computing device is a handheld computing device.

5. The system of claim 2, wherein the prescriber memory further comprises a formulary database and a drug-drug reaction database.

6. The system of claim 1, wherein the procedures further comprise procedures to ascertain a status of the prescription renewal request.

7. The system of claim 6, wherein the procedures further comprise procedures to send the status to the prescriber.

8. The system of claim 1 wherein the dispenser uses a dispenser computing device comprising:
   a processor;
   a communications interface circuit for communicating with the renewal server and the prescriber over the network; and
   a dispenser memory comprising:
      an operating system;
      a dispenser database comprising at least one prescription record comprising:
         patient information;
         the prescribed pharmaceutical;
         an identifier of the prescriber who authorized the prescription;
      prescription filling procedures for checking if refills remain for the prescription and generating a renewal prescription request if not; and
      remote access procedures for transmitting a renewal prescription request to the renewal server and receiving the renewal prescription from the renewal server.

9. The system of claim 8 wherein the dispenser database further comprises of dosage information.

10. The system of claim 1, wherein the database further comprises refill information or dosage information for the prescription.

11. The system of claim 1, wherein the procedures further comprise procedures to notify the patient to contact the prescriber.

12. The system of claim 1, wherein the procedures further comprise:
   procedures to obtain a patient record comprising at least a number of authorized refills of the currently prescribed pharmaceutical; and
   procedures to set a renewal date before a last refill has been consumed by the patient.

13. The system of claim 1, wherein the procedures further comprise:
   procedures to determine whether the pharmaceutical from the prescription is on formulary for the patient; and procedures to dispense the pharmaceutical based on whether the pharmaceutical from the prescription is on formulary for the patient.

14. A method for renewing a prescription for a pharmaceutical via an electronic network, comprising the steps of:

computer monitoring an expiration date of a prescription at a renewal server by periodically determining whether a predetermined time period before the expiration date has been reached;

computer generating a prescription renewal request at the renewal server for renewal of the prescription prior to the expiration date based on the computer monitoring, where said generating occurs without human intervention;

transmitting the prescription renewal request via the electronic network from the renewal server to a client computing device associated with a prescriber, where the prescriber has authority to authorize a dispenser to dispense the prescription;

receiving a renewal prescription at the renewal server, in response to the prescription renewal request; and the renewal server notifying the dispenser to fill the renewal prescription, where the dispenser comprises a pharmacy or pharmacy benefit organization.

15. The method according to claim 14, wherein the receiving further comprises acquiring an appeal from the prescriber for a patient of the prescription to contact the prescriber.

16. The method according to claim 15, wherein the acquiring further comprises notifying the patient to contact the prescriber.

17. The method according to claim 14, wherein the client computing device is a handheld computing device.

18. The method according to claim 14, wherein the method further comprises, prior to the receiving, providing information useful to the prescriber for reviewing the prescription renewal request.

19. The method according to claim 14, wherein the receiving further comprises acquiring the renewal prescription with components that have been changed from the prescription.

20. The method according to claim 14, further comprising deleting the prescription renewal request after a set period of time.

* * * * *